United States Patent [19]

Momin

[11] 4,173,970
[45] Nov. 13, 1979

[54] THERMOGRAPHIC DIAGNOSTIC METHOD AND SYSTEM

[75] Inventor: Abdulmajid U. Momin, Urbana, Ill.

[73] Assignee: Jaymin Research Corporation, Urbana, Ill.

[21] Appl. No.: 821,511

[22] Filed: Aug. 3, 1977

[51] Int. Cl.² ............................................. A61B 5/00
[52] U.S. Cl. .................................. 128/736; 73/343.5
[58] Field of Search .................. 128/2 H, 2 R, 2.1 R; 73/343 R, 343.5

[56] References Cited

U.S. PATENT DOCUMENTS

| | | | |
|---|---|---|---|
| 3,250,126 | 5/1966 | Shapiro | 128/2 H |
| 3,306,282 | 2/1967 | Pierce | 128/2 H |
| 3,651,694 | 3/1972 | Lamb | 128/2 H X |
| 3,782,365 | 1/1974 | Pinna | 128/2 R |
| 3,854,471 | 12/1974 | Wild | 128/2 R X |
| 3,877,463 | 4/1975 | Cary et al. | 128/2 H |
| 3,980,077 | 9/1976 | Shaw | 128/2 H |

Primary Examiner—Lee S. Cohen
Attorney, Agent, or Firm—Burns, Doane, Swecker & Mathis

[57] ABSTRACT

A thermographic diagnostic device which places a visual mark directly on the skin to indicate localized areas exhibiting skin temperatures a predetermined amount above the temperature of the surrounding areas. A hand held probe with a temperature responsive sensing element and marking instrument at one end is placed in contact with the skin and moved across the boy along a desired path. The marking instrument, preferably a pen, is actuated by a control unit when the temperature measured by the sensing element exceeds a preselected temperature relative to surrounding body areas, and a mark is placed on the skin. By moving the probe across the skin in a series of parallel paths, a pattern is placed on the skin corresponding to the localized area of excessive temperature differential.

8 Claims, 3 Drawing Figures

THERMOGRAPHIC DIAGNOSTIC METHOD AND SYSTEM

BACKGROUND OF THE INVENTION

The present invention relates to thermographic diagnostic devices and methods in particular a device and method which detects localized areas on the skin exhibiting temperatures higher than the surrounding area and places a visual indication on the body corresponding to this localized area.

With the life expectancy in advanced countries increasing because of the virtual elimination of infectious disease as a major cause of death, death is mainly caused later in life by arterial diseases and cancer. Although some causes of cancer are known and a few remedies are effective, in many cases the only remedy available is early detection of the cancer followed by surgery, radiation therapy, chemotherapy or a combination of these. The most important factor in successful treatment appears to be early detection of the cancer before it becomes too massive and widespread to be countered.

Breast cancer has become the major cause of death in women aged 35 to 54. Early detection is of primary importance in breast cancer, as the extent of surgery depends on how much the cancer has spread. If detected early enough, simple surgery may be sufficient, but late detection may result in death or require radical and sometimes disfiguring surgery.

The major methods of detection of breat cancer used today are clinical examination by the physician, X-rays (mammography and xero-radiography) and Thermography. In clinical examinations, the breast is examined manually for lumps. If a lump is detected a biopsy is required to determined if the lump is malignant or benign. The cost of this method relative to the others is low, but the accuracy is also low.

In the mammography method, an X-ray examination of the breast is made from different angles and the presence of opacities is indicative of lesions. A positive mammogram is usually followed by a biopsy. The relative cost of this method is high, and the accuracy is high, but repeated examinations cannot be made because of the radiation hazard inherent in X-rays.

It is an object of this invention to provide a novel thermographic method and system for detecting breast cancer and other pathological conditions, which method and system is noninvasive and thus causes no damage to the body and can be repeated as many times as desired without harmful affects.

Thermography is based on the observation that malignant tumors and some other pathological conditions (e.g. arthritic joints, etc.) reveal their presence by localized hot areas of the skin in the vicinity of the tumor or abnormality. Thermographic equipment currently in use are highly sophisticated infrared scanning systems which produce a thermal image of the part of the body being examined. The thermal image is displayed on a cathode-ray tube screen and can be photographed for a permanent record. Examples of these systems are shown in U.S. Pat. Nos. 3,531,642 and 3,430,045.

U.S. Pat. No. 3,335,716 is an example of another method in which the body is coated with a phosphor that is excited to luminescence with ultraviolet radiation and a thermal pattern is displayed on a television tube. The relative accuracy of infrared or ultra-violet thermography for diagnosis of breast cancer is comparable to that of mammography. But, the image produced may not be accurate if heat sources or air currents in the room alter the thermal pattern produced on the surface of the body. Thus, elaborate chambers, free of drafts, heat producing lighting, and the like may be required for accurate work using infrared techniques.

It is accordingly an object of this invention to provide a novel thermographic detecting method and system which is relatively more accurate and inexpensive compared to the foregoing methods and systems.

It is another object of this invention to provide a novel method and system that detects and records localized hot areas of the skin without the inaccuracy of the infra-red method caused by air drafts and other ambient conditions.

Another system for detecting temperature variations on the skin involves the use of a temperature sensitive probe placed in contact with the skin. Examples of such systems are shown in U.S. Pat. Nos. 3,306,282, 3,751,694, 3,933,149, and 3,980,073. Direct contact of a temperature probe to the skin avoids the difficulties caused by air currents and skin surface evaporation in infra-red systems. But all direct contact prior art systems directed specifically to thermography require a special means for recording the measured temperature patterns, and further complications and possibilities for inaccuracies are typically introduced by such devices.

It is a further object of this invention to provide a novel thermographic diagnosing method and system which eliminates the recording inaccuracies and complications in prior art direct contact thermographic systems.

It is a more specific object of this invention to provide a novel method and system for detecting temperature variations on the skin which includes a probe containing a temperature responsive sensing element on one end of the probe for contact with the skin, and a marking device for placing a visual indication directly on the skin itself in the vicinity of the sensing element when a localized hot area has been detected.

In accordance with the present invention, abnormal conditions in the human body that are manifested by areas exhibiting skin temperatures above a predetermined value in relation to surrounding areas of the body (e.g. cancer), are detected and their locations are accurately recorded. A temperature responsive sensing element disposed for contact with the skin surface of an area of the human body provides a signal related to skin temperature at the location of contact. A marking means actuable between a marking and non marking condition selectively places a visual indication on the body in the vicinity of the sensing element when actuated in response to the temperature related signal exceeding a preselected value. In the preferred embodiment of this invention the marking means is a pen or other marking instrument contained in a hand held probe adjacent to the temperature sensing element. The pen is movable between an extended marking position and a retracted non-marking position. The pen is placed in the marking position when the temperature signal generated by the sensing element exceeds a preselected reference signal.

The present invention also relates to a method for diagnosing abnormal conditions in the human body that are manifested by an area exhibiting skin temperatures above a predetermined value in relation to surrounding areas of the body. The steps of the method include contacting a first location of a selected area of the body with a temperature responsive sensing element which generates a signal related to the temperature at that first location, moving the sensing element across the selected area along a desired path, comparing a reference signal with the signal produced by the sensing element as it is moved along the desired path, and marking locations on the body when the comparison indicates that a predetermined temperature differential has been exceeded.

The foregoing and other objects and advantages of the present invention will become apparent to one skilled in the art to which the invention pertains from the following detailed description when read in conjunction with the appended drawings.

DETAILED DESCRIPTION

A preferred embodiment of the thermographic diagnostic apparatus according to the present invention will be described with reference to the FIGS. 1-3.

Figure 1:
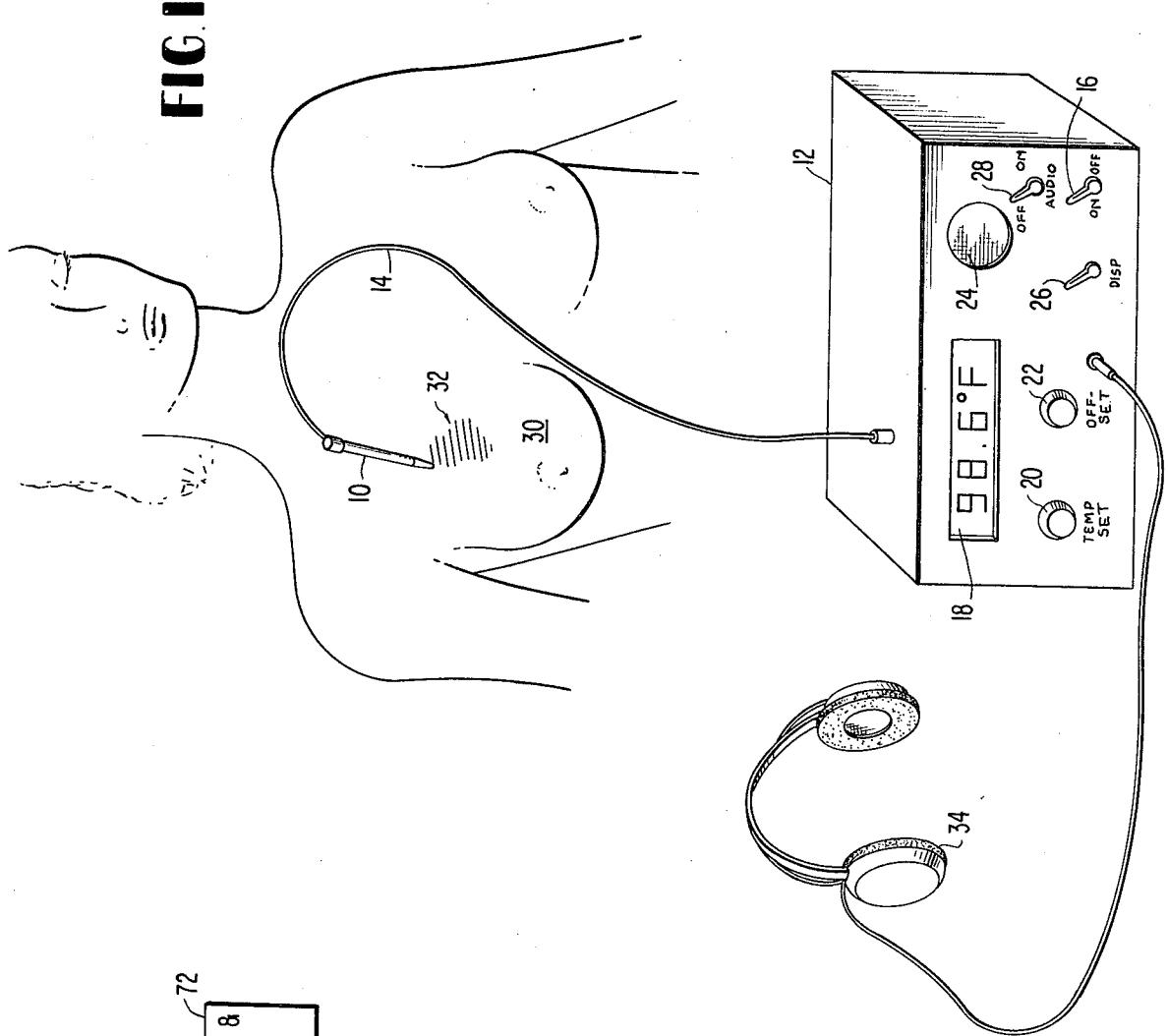
FIG. 1 is a pictorial illustration of a preferred embodiment of the present invention in operation.

FIG. 1 illustrates the present invention in the operation of detecting skin areas on the human body exhibiting temperatures above the temperature of the surrounding area, referred to hereinafter as hot spots. A hand held probe 10 is connected to a control unit 12 by way of a four conductor cable 14. As will be described hereinafter in greater detail, the probe 10 carries a temperature responsive sensing element and a marking means for placing visual marks on the body. The temperature responsive sensing element generates a signal related to sensed temperature and supplies this signal to the control unit 12 over the cable 14. The marking means is controlled by the control unit 12 as a function of sensed temperature by a signal supplied over the cable 14.

With continued reference to FIG. 1, the control unit 12 preferably contains an ON/OFF switch 16, a digital display 18, a Temperature Select control 20, an Off-Set control 22, a speaker 24, a display switch 26 and an audible mode switch 28. A set of headphones 34 may be connected to a conventional output jack to receive an audible signal from the control unit as described hereinafter.

As already mentioned, hot spots on the human body which may be indicative of pathological condition in the body immediately beneath the hot spot are detected and marked in accordance with the invention. To detect these hot spots, the Temperature Select control 20 is set to a value related to the normal skin temperature in an area of the body. More specifically, the temperature sensing element in the probe 10 is placed in contact with the body in the vicinity of the area to be tested. The temperature is noted at that point and the Temperature Select control 20 is adjusted until a temperature reference signal exceeding the noted temperature signal by a predetermined amount (e.g. 1 to 2 degrees) is set.

After the temperature reference has been set, the probe 10 is placed in contact with the body and slowly moved along a desired path. Whenever the skin temperature measured by the temperature responsive sensing element in the probe 10 exceeds by a certain amount the temperature of the surrounding "cooler" areas, the marking means in the probe 10 is actuated and a visual mark is placed on the body.

In the preferred embodiment, the Temperature Select control 20 is set at a value several degrees above the temperature of the cooler areas, and the control unit activates the marker means when the actual skin temperature measured by the temperature sensing element in the probe 10 is greater than or equal to the selected temperature. As an example, assume the body temperature in the area indicated generally by 30 in FIG. 1 is 98° F., and the Temperature Select control 20 is set at 100° F. As the probe 10 is moved across the body, the marking means will be actuated whenever the sensed body temperature reaches or exceeds 100° F.

In FIG. 1, the area of lines indicated generally at 32 shows the markings made by the probe 10 as it is scanned across the area. The markings 32 indicate an area of the body with a temperature greater than or equal to 100° F. A photograph of the markings 32 may be taken to preserve the information for later use. The invention thus provides an accurate record of the location and extent of hot spots on the body by marking these spots directly on the body.

The display switch 26 on the control unit 12 controls the digital display 18 such that in one mode, the temperature value of the reference signal set by the Temperature Select control 20 is displayed, and, in the other mode, the temperature value of the signal produced by the sensing element in the probe 10 is displayed. The temperature offset control 22 is provided to bring different temperature regions within the operating range of the instrument. It should be understood that the absolute values of the measured and reference temperature signals need not be accurately displayed, it being sufficient that their relative values be accurately produced and compared.

A speaker 24 and headphones 34 may be provided in the control unit to provide an audible signal of varying frequency corresponding to the changes in temperature of the skin. A signal related in frequency to the amount the sensed temperature exceeds the preselected temperature may be provided to the speaker 24 and headphones 34 as will be hereinafter described in greater detail. An audio switch 28 may be provided to place the control unit 12 in this audible mode.

Figure 2:
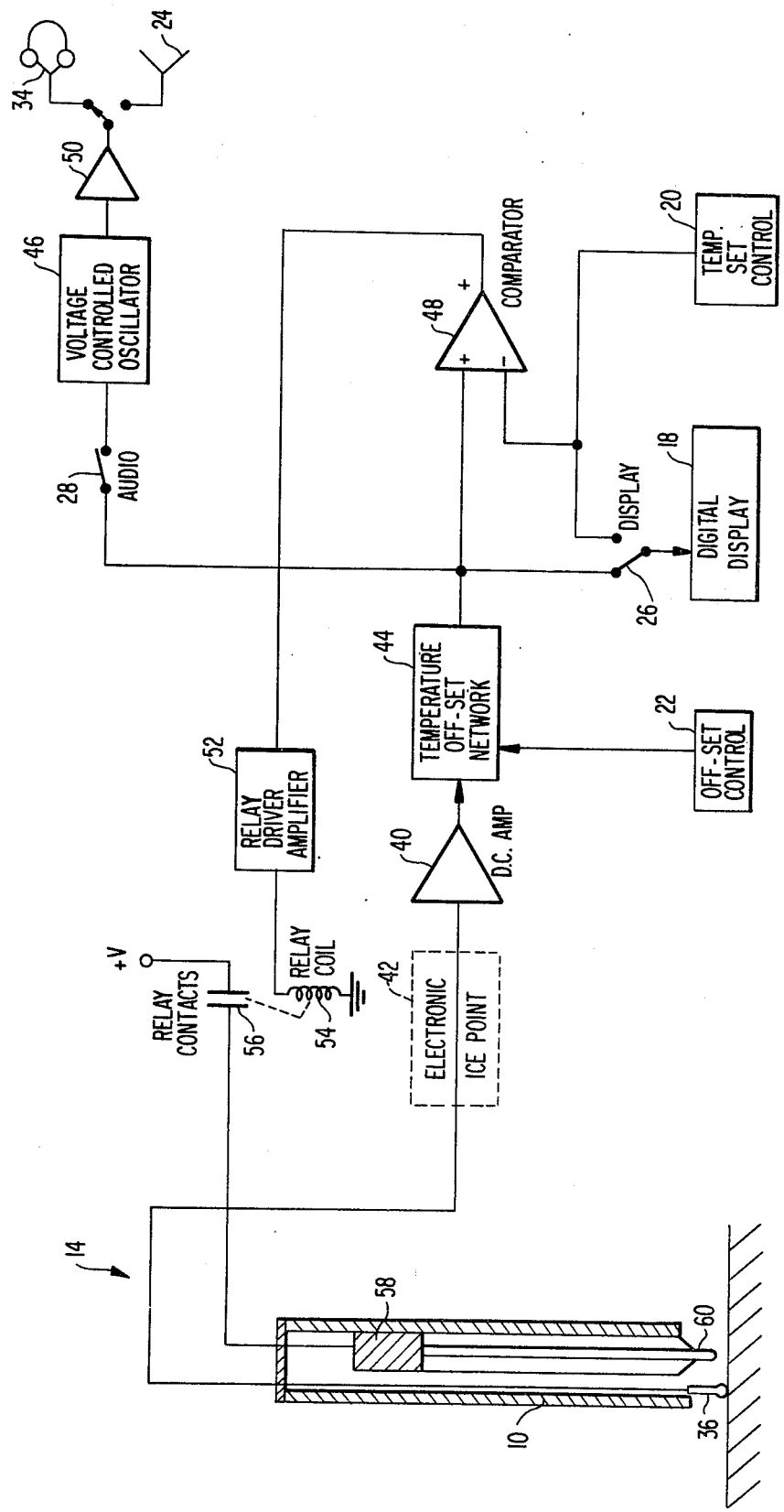
FIG. 2 is a cross-sectional view of a probe and a block diagram of the electronics and control logic according to a preferred embodiment of the invention.

FIG. 2 illustrates in greater detail the preferred embodiment of the electronics and control logic contained within the control unit 12. With reference to FIG. 2, the probe 10 preferably contains a temperature sensor 36 such as a thermocouple with a low thermal capacity and short time constant. It will be appreciated by one skilled in the art that the thermal capacity and time constant of the temperature sensor 36 determines the reaction time of the sensor to temperature changes. If the sensor has a high thermal capacity and a long time constant, it will react slowly to temperature changes and must therefore be moved very slowly across the surface of the body in order for the output signal to accurately reflect the temperature at the contact point. Accordingly, a small thermocouple or similar sensor with a low thermal capacity and short time constant is preferably employed so that the probe may be moved across the surface of the body with an even, moderately fast scanning movement.

The temperature sensor 36 preferably generates an electrical signal linearly proportional to the temperature of the skin in contact with it, but it should be understood that any suitable sensing element which provides an electrical signal related to sensed temperature may be used in this invention. For example, a temperature sensor providing a signal nonlinearly related to sensed temperature may be employed. However, it will be appreciated that the non-linearities of the temperature signal may greatly increase the complexity of the circuitry in the control unit 12.

The signal produced by the temperature sensor 36 is supplied to a suitable conventional d.c. amplifier 40 through the cable 14. A conventional electronic ice point circuit 42 may be provided ahead of the d.c. amplifier 40 in order to appropriately reference the signal from the temperature sensor 36 if a thermocouple is employed as the temperature sensor.

The output signal from the d.c. amplifier 40 is applied to a temperature off-set network 44. The off-set network 44 also receives a signal from the off-set control 22, e.g. a reference signal from a potentiometer, and the network 44 conventionally provides a temperature output signal off-set by an amount determined by the off-set control 22. Of course, other conventional circuitry may be utilized to provide a calibrated temperature reference signal.

The temperature output signal from the off-set network 44 is supplied through the display switch 26 to the input terminal of the digital display 18, through the audio switch 28 to the control input terminal of a conventional voltage controlled oscillator 46 and to the positive input terminal of a conventional voltage comparator 48. The output signal from the voltage controlled oscillator 46 is supplied through an amplifier 50 either directly to the headphones 34 and the speaker 24 or, as illustrated, through a selector switch which allows selective application of the oscillator output signal to either the headphones or the speaker.

The temperature set control 20 supplies a temperature reference signal (e.g. from a potentiometer) to one contact of the switch 26 and to the negative or minus input terminal of the comparator 48. The output signal from the comparator 48 is applied to a conventional relay driver amplifier 52 which drives a relay coil 54. A set of relay contacts 56 associated with the relay coil 54 is connected to a source of voltage (the positive power supply V+). The source of voltage is connected via the cable 14 to a solenoid 58 that controls a marking means 60 in the probe 10.

In accordance with the preferred embodiment of the invention, the marking means 60 is a pen (e.g. a felt tipped pen) controlled between extended and retracted positions by the solenoid 58. As is shown in FIG. 3, the barrel of a suitable pen 62 extends through the probe 10 to the end adjacent the temperature sensor 36. The pen 62 is fixed to a solenoid plunger 64 surrounded by a coil 66. A spring 70 abuts a shoulder 68 on the upper end of the plunger 64 biasing the plunger and the pen 62 into the retracted position. The ends of the solenoid coil 66 are connected respectively to one side of the relay contacts 56 and to the return or common side of the supply V, with the positive side of the supply connected to the other side of the contacts 56 as previously described.

Figure 3:
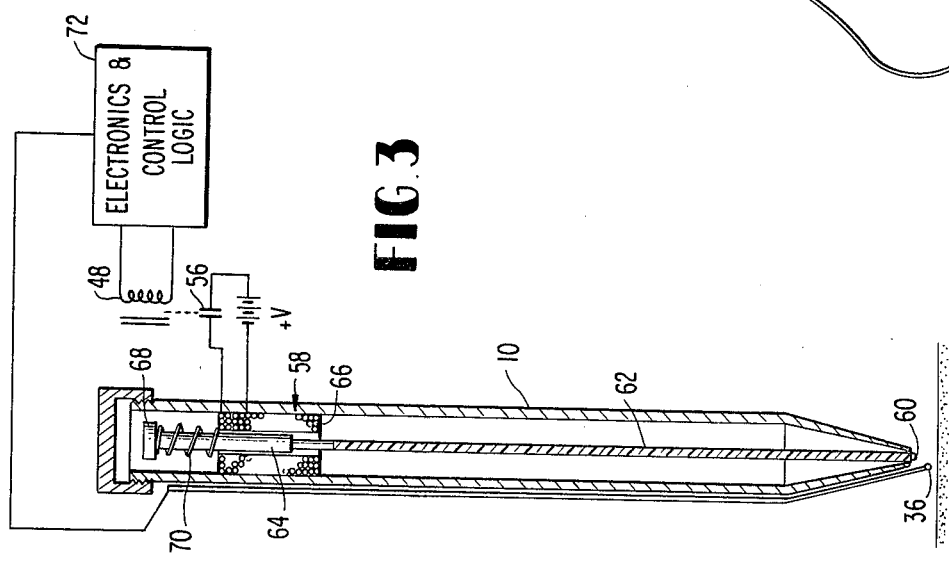
FIG. 3 is a cross-sectional view of one embodiment of the hand held probe of FIG. 1.

In operation, and with reference to FIGS. 2 and 3, the signal produced by the temperature sensor 36 is amplified and supplied to the off-set network 44. With the display switch 26 in the illustrated position, this temperature signal is displayed by the digital display 18 and, assuming that the probe is in contact with the body of the patient, the off-set control can be adjusted for a suitable reading (e.g. 98.6° F.).

The display switch 26 is then changed in position to apply the reference signal from the temperature set control 20 to the display 18. The temperature set control 20 is then manipulated to produce a reading on the display that is a predetermined amount higher than the temperature reading previously displayed. For example, if the temperature signal from the sensor 36 produces a reading of 98.6° F., the temperature reference signal may be adjusted to produce a reading 1.5° to 2.0° higher (e.g. 100.1° F.).

The temperature display switch 26 may then be placed back into its illustrated position and the probe 10 may be moved across the area of the patient's body that is of interest. As the probe 10 is moved across the patient's body with the temperature sensor in contact therewith, the pen 62 remains in the retracted position until an area exceeding the predetermined temperature differential is encountered. When the temperature differential is exceeded, the amplified temperature signal from the sensor 36 exceeds the reference signal from the temperature set control 20, producing a positive output signal from the comparator 48.

The positive output signal from the comparator 48, triggers the relay driver switch 52, actuating the relay coil 54 and closing the relay contacts 56. The closing of the relay contacts 56 actuates the solenoid 58 by passing a current through the solenoid coil 66. This forces the plunger 64 of the solenoid in a downward direction, moving the pen 62 from its non-marking, retracted condition to its marking, extended condition. When the temperature signal from the sensor 36 drops below the temperature reference signal, the relay coil is deenergized which in turn deenergizes the solenoid 58, and the pen 62 is returned to its retracted position by the spring 70.

It can thus be appreciated that the invention provides a simple yet very accurate method of determining and recording the location of abnormal body conditions that are exhibited as hot spots on the surface of the body. As the probe 10 is moved across the surface of the body in contact therewith, differences in surface temperature are sensed and produce markings on the surface of the body when a predetermined differential is exceeded. The differential causing the markings can be adjusted so as to prevent the marking of normal "warm spots" (e.g. blood vessels), and the temperature variations can be simultaneously indicated audibly, by a variable pitch note.

In this connection, the output signal from the temperature off-set network 44 may be supplied through the audio switch 28 to the voltage controlled oscillator 46 to provide an audio signal whose frequency varies directly with the temperature sensed by the sensing element 36. For example, the audio signal may be at zero or a very low frequency at normal temperature and may increase in frequency with increasing temperature. This permits the operator to listen (through the speaker or headphones) while scanning the area of the body of interest. Any noticeable frequency changes may be noted and those areas exhibiting such changes may be reexamined using a lower temperature differential to actuate the marking means, if desired.

In the preferred embodiment, the temperature set control 20 is set at a temperature above the normal skin temperature and the marking means is actuated when the sensed temperature is greater than or equal to this selected temperature, but other methods of comparing signals may be used as long as the marker means 38 is actuated to indicate a measured temperature above that of the surrounding area by some predetermined amount. Moreover, although a felt tipped pen actuated by a solenoid is the preferred marking means, other devices such as an ink spray nozzle actuated by an electrical signal may be used as long as a mark is made on the skin in the vicinity of the sensing element 36. The marking means 60 could also be separate from the probe although it is preferable to have both the marking means 38 and the sensing element 36 in a convenient hand held probe 10.

The present invention may be embodied in other specific forms without departing from the spirit or essential characteristics thereof. The present disclosed embodiment is therefore to be considered in all respects as illustrative and not restrictive, the scope of the invention being indicated by the appended claims rather than be the foregoing description, and all changes which come within the meaning and range of equivalency of the claims are therefore intended to be embraced therein.

What is claimed is:

1. Apparatus for diagnosing pathological conditions in the human body that are manifested by an area exhibiting skin temperatures above a predetermined value in relation to surrounding areas, the apparatus comprising:
    a hand held probe having a temperature responsive sensing element disposed at one end for contact with the skin surface of an area of the human body for providing a signal related to skin temperature at the location of contact;
    a marking pen carried by said hand held probe adjacent the temperature responsive sensing element and movable between a retracted non-marking position and an extended marking position wherein said marking pen is biased into contact with the skin surface for selectively placing a visual indication on the skin at the approximate location of contact between the skin surface and the sensing element; and
    means for biasing and holding said marking pen in contact with the skin surface in response to the temperature related signal exceeding a preselected value.

2. The apparatus of claim 1, wherein said biasing and holding means comprises a solenoid mounted on said marking pen which is actuated by said temperature related signal exceeding said preselected value, and said hand held probe comprises a hollow tubular member having an opening at said one end thereof with said temperature responsive sensing element being disposed adjacent said opening and said marking pen and solenoid being disposed within said tubular member wuch that when said marking pen is biased into its extended position said marking pen extends beyond the opening of said tubular member into contact with the skin surface.

3. Apparatus for diagnosing pathological conditions in the human body that are manifested by an area exhibiting skin temperatures above a predetermined value in relation to surrounding areas, the apparatus comprising:
    a hand held probe with a temperature responsive sensing element disposed at one end for contact with the skin surface of an area of the human body to provide a signal related to skin temperature at the location of contact;
    a marker pen carried by said hand held probe adjacent the temperature responsive sensing element and movable between an extended marking position and a retracted non-marking position wherein said marker pen is biased into contact with the skin surface, said marker pen being operative to place a visual indication on the skin surface at the approximate location of contact between the surface and the sensing element in only the extended position of the marker;
    means for generating a reference signal related to a preselected temperature;
    means responsive to the reference signal and the temperature related signal generated by the temperature sensing element for generating an actuating signal when a predetermined relationship exists between the reference signal and the temperature related signal; and
    means responsive to the actuating signal for biasing and holding said marker pen in contact with the skin surface for the duration of said actuating signal.

4. The apparatus of claim 3, wherein said biasing and holding means comprises a solenoid mounted on said marker pen and activated by said actuating signal, and said hand held probe comprises a hollow tubular member having an opening at said one end thereof with said temperature responsive element being disposed adjacent said opening and said marker pen and solenoid being disposed within said tubular member such that when said solenoid is activated and biases said marker pen into its extended position, said marker pen extends beyond the opening of said tubular member into contact with the skin surface.

5. Apparatus for diagnosing pathological conditions in the human body that are manifested by an area exhibiting skin temperatures above a predetermined value in relation to surrounding areas, the apparatus comprising:
    a hand held probe comprising a hollow tubular member having an opening at one end thereof and a temperature responsive sensing element disposed adjacent said opening for contact with the skin surface of an area of the human body to provide a signal related to skin temperature at the location of contact;
    a marking pen mounted within said tubular member, said marking pen being movable between a retracted non-marking position and an extended marking position wherein said marking pen extends beyond the opening of said tubular member into contact with the skin surface at the approximate location of contact between the skin surface and the sensing element for selectively placing a visual indication on the skin;
    means for generating a reference signal related to a preselected temperature;
    means responsive to the reference signal and the temperature related signal generated by the temperature sensing element for generating an actuating signal when a predetermined relationship exists between the reference signal and the temperature related signal; and
    a solenoid mounted within said tubular member and activated by said actuating signal which biases and holds said marking pen in contact with the skin surface for the duration of said actuating signal.

6. The apparatus of claim 5, wherein said tubular member comprises a converging section at the end of said tubular member containing said opening and said temperature responsive sensing element follows the contour of said converging section and extends beyond said converging section adjacent the opening of said tubular member.

7. A method for diagnosing pathological conditions in the human body that are manifested by a skin area exhibiting temperatures above a predetermined value in relation to surrounding areas of the body, the method comprising the steps of:

contacting a first location of a selected area of the body with a temperature responsive sensing element by hand to generate a signal related to the temperature at that first location;

providing a temperature reference signal representing a temperature of pre-selected greater value than the temperature at the first location;

moving the temperature sensing element by hand across the selected area along a desired path;

comparing the reference signal with the signal produced by the sensing element as the sensing element is moved by hand along the desired path; and forming a continuous visual indication on the body corresponding only to those locations where the comparison indicates that a predetermined temperature differential has been exceeded simultaneous with the step of moving said temperature sensing element across the selected area of the body.

8. The method of claim 4 wherein the temperature responsive sensing element has a temperature reaction time lag characteristic below a predetermined value and the sensing element is moved along the desired path at a rate related to the temperature reaction time lag characteristic of the sensing element.

* * * * *